(12) United States Patent
Tsubokura et al.

(10) Patent No.: US 9,096,502 B2
(45) Date of Patent: Aug. 4, 2015

(54) PRODUCTION PROCESS FOR FLUOROSULFONYLIMIDE AMMONIUM SALT

(75) Inventors: Shiro Tsubokura, Joetsu (JP); Yasuyuki Aiura, Joetsu (JP); Toru Suzuki, Joetsu (JP); Michiaki Maruyama, Joetsu (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 14/001,547

(22) PCT Filed: Feb. 24, 2012

(86) PCT No.: PCT/JP2012/054566
§ 371 (c)(1),
(2), (4) Date: Aug. 26, 2013

(87) PCT Pub. No.: WO2012/117961
PCT Pub. Date: Sep. 7, 2012

(65) Prior Publication Data
US 2013/0331609 A1 Dec. 12, 2013

(30) Foreign Application Priority Data
Mar. 3, 2011 (JP) ................................. 2011-046738

(51) Int. Cl.
*C07C 311/48* (2006.01)
*C07C 303/40* (2006.01)
*C01B 21/093* (2006.01)
*H01M 10/052* (2010.01)
*H01M 10/0568* (2010.01)
*C01B 21/092* (2006.01)

(52) U.S. Cl.
CPC ............ *C07C 311/48* (2013.01); *C01B 21/093* (2013.01); *C01B 21/0923* (2013.01); *C07C 303/40* (2013.01); *H01M 10/052* (2013.01); *H01M 10/0568* (2013.01); *Y02E 60/122* (2013.01)

(58) Field of Classification Search
CPC .. C01B 21/0923; C01B 21/093; C07C 303/40; C07C 311/48; H01M 10/10; H01M 10/052; H01M 10/0568
USPC .......................................................... 564/82
See application file for complete search history.

(56) References Cited

U.S. PATENT DOCUMENTS 3,882,128 A * 5/1975 McLaren et al. .............. 525/420
5,916,475 A 6/1999 Michot et al.

FOREIGN PATENT DOCUMENTS

| JP | A-8-511274 | 11/1996 |
|---|---|---|
| JP | 2009-292728 | * 12/2009 |
| JP | A-2010-168249 | 8/2010 |
| JP | A-2010-168308 | 8/2010 |
| SG | 192258 A1 | 9/2013 |
| WO | WO 2009/123328 A1 | 10/2009 |
| WO | WO 2010/010613 A1 | 1/2010 |

OTHER PUBLICATIONS

Han et al., "Lithium bis(fluorosulfonyl)imide (LiFSI) as conducting salt for nonaqueous liquid electrolytes for lithium ion batteries: Physichemical and electrochemical properties," Journal of Power Sciences, 196, 3623-3632, 2011.*
Translation of JP2009-292728.*
Translation of WO2010010613.*
Supplementary Search Report issued in European Patent Application No. 12 75 2317.3 dated May 23, 2014.
Růžička et al., "Zur Synthese von Ammonium-imido-bis(schwefelsäura-fluorid) $NH_4N(SO_2F)_2$," Z. Chem., 1987, vol. 27, No. 6, pp. 227-228 (with translation).
Ruff et al., "Imidodisulfuryl Fluoride, Cesium Imidodisulfuryl Fluoride, and Fluoroimidodisulfuryl Fluoride," Inorganic Synthesis, 1968, vol. 11, pp. 138-140.
Krumm et al., "Synthesis of Poly- and the First Perfluoroalkyl-$N(SO_2F)_2$ Derivatives: Improved Methods for the Preparation of $XN(SO_2F)_2$ (X = H, Cl) and Single-Crystal Diffraction Studies of $HN(SO_2Cl)2$, $HN(SO_2F)_2$, and $CF_3CH_2N(SO_2F)_2$," Inorg. Chem., 1998, vol. 37, pp. 6295-6303.
Beran et al., "A New Method of the Preparation of Imido-bis(sulfuric acid) Dihalogenide, (F,Cl), and the Potassium Salt of Imido-bis-(sulfuric acid) Difluoride," Z. Anorg. Allg. Chem., 2005, vol. 631, pp. 55-59.
Appel et al., "Über die Reaktion von Sulfuryl-di-isocyanat mit Halogeno-schwefelsäuren. Ein einfaches Verfahren zur Herstellung von Fluor-sulfonylisocyanat und Imido-bis-schwefelsäurefluorid," Chemische Berichte, 1964, vol. 97, pp. 849-850 (with translation).
International Search Report issued in International Patent Application No. PCT/JP2012/054566 dated May 29, 2012 (with translation).
Written Opinion issued in International Patent Application No. PCT/JP2012/054566 dated May 29, 2012 (with translation).
Jul. 16, 2014 Office Action issued in Singapore Application No. 2013057930.

* cited by examiner

*Primary Examiner* — Paul A Zucker
*Assistant Examiner* — Mark Luderer
(74) *Attorney, Agent, or Firm* — Oliff PLC

(57) ABSTRACT

A compound [II] such as ammonium N,N-di(fluorosulfonyl)imide is obtained by reacting a compound [I] such as N,N-di(chlorosulfonyl)imide and $NH_4F$ $(HF)_p$. A compound [IV] such as an N,N-di(fluorosulfonyl)imide alkali metal salt is obtained by reacting the obtained compound [II] and an alkali metal compound or the like.

4 Claims, No Drawings

US 9,096,502 B2

PRODUCTION PROCESS FOR FLUOROSULFONYLIMIDE AMMONIUM SALT

TECHNICAL FIELD

The present invention relates to a process for producing a fluorosulfonylimide ammonium salt. More specifically, the present invention relates to a process for producing a fluorosulfonylimide ammonium salt with good efficiency and maximum suppression of the contamination of metal impurities that degrade electrolyte properties and the like.

Priority is claimed on Japanese Patent Application No. 2011-046738, filed Mar. 3, 2011, the content of which is incorporated herein by reference.

BACKGROUND ART

Fluorosulfonylimide salts are useful compounds in a wide variety of fields, and are used as electrolytes, as additives added to the electrolytes of fuel cells, and as selective electron withdrawing materials and the like (see Patent Document 1). Fluorosulfonylimide alkali metal salts and various fluorosulfonylimide onium salts can be obtained by cation exchange reactions using an alkali metal compound or an onium compound. Fluorosulfonylimide ammonium salts are useful as production intermediates for fluorosulfonylimide alkali metal salts and fluorosulfonylimide onium salts other than ammonium salts.

Various methods have been proposed for synthesizing fluorosulfonylimide ammonium salts. For example, Non-Patent Document 1 discloses a method of synthesizing a di(fluorosulfonyl)imide ammonium salt from di(fluorosulfonyl)imide and ammonia.

Patent Document 2 discloses a method of synthesizing a bis[di(fluorosulfonyl)imide] onium salt by reacting di(chlorosulfonyl)imide with an onium compound to obtain a chlorosulfonyl)imide onium salt, and then reacting this onium salt with a fluoride containing at least one element selected from the group consisting of elements of group 11 to group 15 and elements in the fourth to sixth periods (but excluding arsenic and antimony). Examples disclosed for the fluoride used in the production process described in Patent Document 2 include zinc fluoride ($ZnF_2$), copper fluoride ($CuF_2$) and bismuth fluoride ($BiF_2$). These compounds are all solid substances at normal temperature.

Further, Non-Patent Documents 2 and 3 disclose a method of directly synthesizing di(fluorosulfonyl)imides from di(chlorosulfonyl)imides using arsenic trifluoride ($AsF_3$) or antimony trifluoride ($SbF_3$) as a fluorinating agent.

DOCUMENTS OF RELATED ART

Patent Documents

Patent Document 1: Published Japanese Translation No. Hei 08-511274 of PCT
Patent Document 2: Japanese Unexamined Patent Application, First Publication No. 2010-168308

Non-Patent Documents

Non-Patent Document 1: Zeitschrift fuer Chemie (1987), 27(6), 227 to 228
Non-Patent Document 2: John K. Ruff and Max Lustig, Inorg. Synth., 11, 138 to 140 (1968)
Non-Patent Document 3: Jean'ne M. Shreeve et al., Inorg. Chem., 1998, 37(24), 6295 to 6303

DISCLOSURE OF INVENTION

Problems to be Solved by the Invention

The di(fluorosulfonyl)imide used as a starting material in the synthetic method disclosed in Non-Patent Document 1 can be obtained by treating and freeing a di(fluorosulfonyl)imide salt with a strong acid. However, because di(fluorosulfonyl)imide is itself a strong acid, industrial production is not easy. A method of synthesizing di(fluorosulfonylimide) using an ion exchange resin exists, but the steps are complex, and it is not suitable for industrial production.

In the synthetic method disclosed in Patent Document 2, because the metal element derived from the fluoride causes a deterioration in the electrolyte properties, the metal element derived from the fluoride must be removed. In order to completely remove the metal element, a complex refining operation must be performed.

The $AsF_3$ used in the synthetic method disclosed in Non-Patent Document 2 or 3 is comparatively expensive. Both As and Sb are elements that exhibit a high level of toxicity, and therefore workability is problematic. Particularly in the case of the synthetic method using $AsF_3$, compounds that are difficult to separate from the target product are produced as by-products. As a result, the synthetic method disclosed in Non-Patent Documents 2 and 3 is unsuitable for industrial production.

An object of the present invention is to provide a process for producing a fluorosulfonylimide ammonium salt with good efficiency and maximum suppression of the contamination of metal impurities that degrade electrolyte properties and the like, and also to provide a process for producing a fluorosulfonylimide salt containing no metal impurities that degrade electrolyte properties and the like from a fluorosulfonylimide ammonium salt.

Means to Solve the Problems

The inventors of the present invention undertook intensive investigations in order to achieve the above object. As a result, they discovered that by reacting a specific chlorosulfonylimide with a fluorinating agent represented by $NH_4F$ $(HF)_p$ (wherein p represents a real number of 0 to 10), a fluorosulfonylimide ammonium salt could be synthesized in an industrially simple manner. Further, they also discovered that by subjecting the thus obtained fluorosulfonylimide ammonium salt to a cation exchange under the action of a metal compound or the like, a fluorosulfonylimide metal salt or the like containing no metal impurities that degrade electrolyte properties and the like could be obtained. The present invention was completed on the basis of these findings.

In other words, the present invention includes the following aspects.

(1) A process for producing a fluorosulfonylimide ammonium salt represented by formula [II] (hereafter also referred to as "compound [II]"), the method including reacting a compound represented by formula [I] (hereafter also referred to as "compound [I]") and a fluorinating agent represented by formula [III] (hereafter also referred to as "fluorinating agent [III]").

(2) A process for producing a fluorosulfonylimide salt represented by formula [IV] (hereafter also referred to as "compound [IV]"), the method including reacting the fluorosulfonylimide ammonium salt represented by formula [II]

obtained by the method disclosed above in (1) with at least one compound selected from the group consisting of metal compounds, onium compounds and organic amine compounds.

(3) The process for producing a fluorosulfonylimide salt disclosed above in (2), wherein the at least one compound is selected from the group consisting of alkali metal compounds, onium compounds and organic amine compounds.

[Chemical Formula 1]

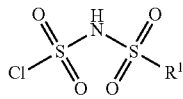

[I]

In formula [I], $R^1$ represents a fluoroalkyl group having 1 to 6 carbon atoms, a fluorine atom, or a chlorine atom.

[Chemical Formula 2]

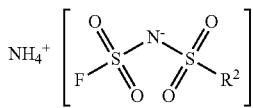

[II]

In formula [II], $R^2$ represents a fluoroalkyl group having 1 to 6 carbon atoms, or a fluorine atom.

[Chemical Formula 3]

  [III]

In formula [III], p represents a real number of 0 to 10.

[Chemical Formula 4]

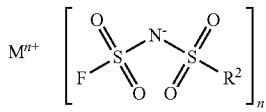

[IV]

In formula [IV], $M^{n+}$ represents a metal cation or an onium cation (excluding $NH_4^+$), n corresponds with the valency of the metal cation or the onium cation (excluding $NH_4^+$) and is an integer of 1 to 4, and $R^2$ is the same as defined above in formula [II].

Effects of the Invention

The present invention enables a fluorosulfonylimide ammonium salt to be manufactured in an industrially efficient manner. Further, by subjecting the thus obtained fluorosulfonylimide ammonium salt to a cation exchange reaction, another fluorosulfonylimide salt containing no metal impurities that degrade electrolyte properties and the like can be manufactured.

EMBODIMENTS OF THE INVENTION (Process for Producing Compound [II])

The process for producing a compound [II] according to the present invention includes a step of reacting a compound [I] and a fluorinating agent [III].

The compound [I] used in the present invention is a compound represented by formula [I].

[Chemical Formula 5]

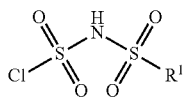

[I]

In formula [I], $R^1$ represents a fluoroalkyl group having 1 to 6 carbon atoms, a fluorine atom, or a chlorine atom. Of these, $R^1$ is preferably a chlorine atom.

The number of carbon atoms constituting the fluoroalkyl group for $R^1$ is from 1 to 6, preferably from 1 to 4, and more preferably from 1 to 2. Examples of the fluoroalkyl group include a fluoromethyl group, difluoromethyl group, trifluoromethyl group, fluoroethyl group, difluoroethyl group, 2,2,2-trifluoroethyl group, pentafluoroethyl group, 3,3,3-trifluoropropyl group, perfluoro-n-propyl group, fluoropropyl group, perfluoroisopropyl group, fluorobutyl group, 3,3,4,4,4-pentafluorobutyl group, perfluoro-n-butyl group, perfluoroisobutyl group, perfluoro-t-butyl group, perfluoro-sec-butyl group, fluoropentyl group, perfluoropentyl group, perfluoroisopentyl group, perfluoro-t-pentyl group, fluorohexyl group, perfluoro-n-hexyl group and perfluoroisohexyl group. Among these groups, a trifluoromethyl group, pentafluoroethyl group or perfluoro-n-propyl group is preferable, and a trifluoromethyl group or pentafluoroethyl group is more preferable.

Specific examples of the compound [I] include N-(chlorosulfonyl)-N-(fluorosulfonyl)imide, di(chlorosulfonyl)imide, N-(chlorosulfonyl)-N-(trifluoromethylsulfonyl)imide, N-(chlorosulfonyl)-N-(pentafluoroethylsulfonyl)imide, and N-(chlorosulfonyl)-N-(perfluoro-n-propylsulfonyl)imide.

The compound [I] may be a commercially available material, or may be synthesized, for example, using the method disclosed in Z. Anorg. Allg. Chem., 2005, 631, 55 to 59. For example, di(chlorosulfonyl)imide, which is one compound represented by formula [I], can be obtained by reacting chlorosulfonyl isocyanate and chlorosulfonic acid (see Chemisch Berichte 1964, 97 849 to 850).

Further, N-(chlorosulfonyl)-N-(fluoroalkylsulfonyl)imides can be obtained by a reaction between chlorosulfonyl isocyanate and a fluoroalkylsulfonic acid, or by a reaction between a fluoroalkylsulfonyl isocyanate and chlorosulfonic acid.

The fluorinating agent [III] used in the present invention is a compound represented by formula [III].

[Chemical Formula 6]

  [III]

In formula [III], p represents a real number of 0 to 10, and is preferably a real number from 0 to 4, and more preferably an integer from 0 to 4. Specific examples of the fluorinating agent [III] include $NH_4F$, $NH_4F$ HF, $NH_4F$ 2HF, $NH_4F$ 3HF, and $NH_4F$ 4HF. Among these compounds, $NH_4F$ and $NH_4F$ HF are preferable.

A commercially available material can be used as the fluorinating agent [III]. Further, $NH_4F$ can be obtained by deposition by passing ammonia through anhydrous hydrogen fluoride. $NH_4F$ can also be obtained by heating and subliming a mixture of ammonium chloride and sodium fluoride.

$NH_4F$ HF, $NH_4F$ 2HF, $NH_4F$ 3HF, and $NH_4F$ 4HF and the like can be obtained by passing ammonia through anhydrous hydrogen fluoride in the required proportion, or can also be obtained by mixing an ammonia aqueous solution with hydrofluoric acid (aqueous solution), and then concentrating the mixture by evaporating off the water. Further, these compounds can also be obtained by thermal decomposition of $NH_4F$. Moreover, they can also be obtained by passing anhydrous hydrogen fluoride through $NH_4F$ HF, $NH_4F$ 2HF or $NH_4F$ 3HF.

The amount used of the fluorinating agent [III] is preferably within a range from 1 mol to 20 mol, more preferably from 1 mol to 10 mol, and still more preferably from 1 mol to 5 mol, per 1 mol of the compound [I].

The reaction between the compound [I] and the fluorinating agent [III] can be conducted within an organic solvent or in the absence of a solvent. There are no particular limitations on the organic solvents that can be used in the reaction, provided they do not impair the fluorination reaction. Examples of the solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methylsulfolane, dimethylsulfoxide, N,N-dimethylformamide, N-methyl oxazolidinone, acetonitrile, valeronitrile, benzonitrile, ethyl acetate, isopropyl acetate, butyl acetate, nitromethane, nitrobenzene, toluene, chlorobenzene, methylene chloride, carbon tetrachloride and chloroform. From the viewpoint of achieving smooth progression of the fluorination reaction, the use of a polar solvent is preferable. Examples of preferred solvents include acetonitrile, ethyl acetate, isopropyl acetate and butyl acetate.

The organic solvent is preferably dewatered prior to use. If water exists, then the compound [I] becomes more prone to decomposition, and therefore there is a possibility that the yield may deteriorate.

The temperature of the fluorination reaction may be adjusted appropriately in accordance with the state of progression of the reaction, but is preferably within a range from −40° C. to 200° C., and more preferably from −20° C. to 100° C. The time required for the reaction varies depending on the reaction scale, but is preferably from 0.1 hours to 48 hours, and more preferably from 0.5 hours to 24 hours.

By using the production process according to the present invention, the compound [II] can be obtained. The compound [II] is a fluorosulfonylimide ammonium salt represented by formula [II].

[Chemical Formula 7]

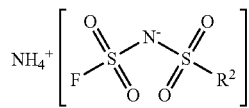

[II]

In formula [II], $R^2$ represents a fluoroalkyl group having 1 to 6 carbon atoms, or a fluorine atom. Examples of the fluoroalkyl group include the same groups as those mentioned above within the description of $R^1$.

Specific examples of the compound represented by formula [II] include ammonium di(fluorosulfonyl)imide, ammonium N-(fluorosulfonyl)-N-(trifluoromethylsulfonyl)imide, ammonium N-(fluorosulfonyl)-N-(pentafluoroethylsulfonyl)imide, and ammonium N-(fluorosulfonyl)-N-(perfluoro-n-propylsulfonyl)imide. Among these, ammonium di(fluorosulfonyl)imide is preferable.

The compound [II] is useful as an intermediate for manufacturing a fluorosulfonylimide salt represented by formula [IV]. Further, the compound [II] is also useful as a material for an ion conductor used in forming primary cells, secondary cells such as a lithium (ion) secondary cell, and electrochemical devices such as electrolytic capacitors, electrical double-layer capacitors, fuel cells, solar cells and electrochromic elements.

(Process for Producing Compound [IV])

The process for producing a compound [IV] according to the present invention includes a step of reacting the compound [II] obtained using the production process described above with at least one compound selected from the group consisting of metal compounds, onium compounds and organic amine compounds (hereafter this reaction is also referred to as a cation exchange reaction).

This cation exchange reaction may be performed by mixing, in the presence of a solvent, the compound [II] and at least one compound selected from the group consisting of metal compounds, onium compounds and organic amine compounds. The at least one compound is preferably selected from the group consisting of alkali metal compounds, onium compounds and organic amine compounds, and is more preferably an alkali metal compound.

There are no particular limitations on the metal compound used in the cation exchange reaction, provided it undergoes a cation exchange reaction with the compound [II], but an alkali metal compound is preferable. Examples of the alkali metal compound include hydroxides such as LiOH, NaOH, KOH, RbOH and CsOH, carbonates such as $Li_2CO_3$, $Na_2CO_3$, $K_2CO_3$, $Rb_2CO_3$ and $Cs_2CO_3$, hydrogen carbonates such as $LiHCO_3$, $NaHCO_3$, $KHCO_3$, $RbHCO_3$ and $CsHCO_3$, chlorides such as LiCl, NaCl, KCl, RbCl and CsCl, bromides such as LiBr, NaBr, KBr, RbBr and CsBr, fluorides such as LiF, NaF, KF, RbF and CsF, alkoxide compounds such as $CH_3OLi$, EtOLi, t-BuOK and t-BuONa, hydrides such as NaH, KH and LiH, and alkyllithium compounds such as i-$Pr_2NLi$, EtLi, BuLi and t-BuLi (wherein Et represents an ethyl group, Pr represents a propyl group and Bu represents a butyl group). Of these compounds, a hydroxide is preferable. By using a hydroxide, ammonia is produced as a by-product in the cation exchange reaction, and therefore by removing this ammonia under reduced pressure, the equilibrium can be adjusted to a state that promotes the cation exchange reaction. By using an alkali metal compound, inorganic salt by-products can be removed by filtration and water washing, meaning the product can be easily purified.

The amount used of the alkali metal compound is preferably from 1 mol to 10 mol, and more preferably from 1 mol to 5 mol, per 1 mol of the compound [II].

Examples of the onium compound used in the cation exchange reaction include nitrogen-based onium compounds such as imidazolium compounds, pyrazolium compounds, pyridinium compounds, pyrrolidinium compounds, piperidinium compounds, morpholinium compounds and quaternary ammonium compounds, phosphorus-based onium compounds such as quaternary phosphonium compounds and tertiary phosphine compounds, sulfur-based onium compounds such as sulfonium compounds, as well as guanidinium compounds, isouronium compounds and isothiouronium compounds. Among these compounds, organic onium compounds are preferable. Further, the onium compound preferably contains no metal elements that degrade electrolyte properties and the like.

Specific examples of the imidazolium compounds include chlorides such as 1,3-dimethylimidazolium chloride, 1-ethyl-3-methylimidazolium chloride, 1-butyl-3-methylimidazolium chloride, 1-hexyl-3-methylimidazolium chloride, 1-octyl-3-methylimidazolium chloride, 1-allyl-3-ethylimidazolium chloride, 1-allyl-3-butylimidazolium chloride, 1,3-diallylimidazolium chloride, 1-ethyl-2,3-dimethylimidazolium chloride, 1-butyl-2,3-dimethylimidazolium chloride and 1-hexyl-2,3-dimethylimidazolium chloride; bromides such as 1,3-dimethylimidazolium bromide, 1-ethyl-3-methylimidazolium bromide, 1-butyl-3-methylimidazolium bromide, 1-hexyl-3-methylimidazolium bromide, 1-octyl-3-methylimidazolium bromide, 1-allyl-3-ethylimidazolium bromide, 1-allyl-3-butylimidazolium bromide, 1,3-diallylimidazolium bromide, 1-ethyl-2,3-dimethylimidazolium bromide, 1-butyl-2,3-dimethylimidazolium bromide and 1-hexyl-2,3-dimethylimidazolium bromide;

iodides such as 1,3-dimethylimidazolium iodide, 1-ethyl-3-methylimidazolium iodide, 1-butyl-3-methylimidazolium iodide, 1-hexyl-3-methylimidazolium iodide, 1-octyl-3-methylimidazolium iodide, 1-allyl-3-ethylimidazolium iodide, 1-allyl-3-butylimidazolium iodide, 1,3-diallylimidazolium iodide, 1-ethyl-2,3-dimethylimidazolium iodide, 1-butyl-2,3-dimethylimidazolium iodide and 1-hexyl-2,3-dimethylimidazolium iodide; and hydroxides such as 1,3-dimethylimidazolium hydroxide, 1-ethyl-3-methylimidazolium hydroxide, 1-butyl-3-methylimidazolium hydroxide, 1-hexyl-3-methylimidazolium hydroxide, 1-octyl-3-methylimidazolium hydroxide, 1-allyl-3-ethylimidazolium hydroxide, 1-allyl-3-butylimidazolium hydroxide, 1,3-diallylimidazolium hydroxide, 1-ethyl-2,3-dimethylimidazolium hydroxide, 1-butyl-2,3-dimethylimidazolium hydroxide and 1-hexyl-2,3-dimethylimidazolium hydroxide.

Specific examples of the pyrazolium compounds include chlorides such as 2-ethyl-1,3,5-trimethylpyrazolium chloride, 2-propyl-1,3,5-trimethylpyrazolium chloride, 2-butyl-1,3,5-trimethylpyrazolium chloride and 2-hexyl-1,3,5-trimethylpyrazolium chloride; bromides such as 2-ethyl-1,3,5-trimethylpyrazolium bromide, 2-propyl-1,3,5-trimethylpyrazolium bromide, 2-butyl-1,3,5-trimethylpyrazolium bromide and 2-hexyl-1,3,5-trimethylpyrazolium bromide; and hydroxides such as 2-ethyl-1,3,5-trimethylpyrazolium hydroxide, 2-propyl-1,3,5-trimethylpyrazolium hydroxide, 2-butyl-3,5-trimethylpyrazolium hydroxide and 2-hexyl-1,3,5-trimethylpyrazolium hydroxide.

Specific examples of the pyridinium compounds include 1-acetonylpyridinium chloride, 1-aminopyridinium iodide, 2-benzyloxy-1-methylpyridinium trifluoromethanesulfonate, 1,1'-[biphenyl-4,4'-diylbis(methylene)]-bis(4,4'-bipyridinium) bis(hexafluorophosphate), 1,1'-[biphenyl-4,4'-diylbis(methylene)]-bis(4,4'-bipyridinium)dibromide, 1,1'-bis(2,4-dinitrophenyl)-4,4'-bipyridinium dichloride, bis(2,4,6-trimethylpyridine)bromonium hexafluorophosphate, 2-bromo-1-ethylpyridinium tetrafluoroborate, 4-bromopyridine hydrobromide, 4-bromopyridine hydrochloride, 1-butyl-4-methylpyridinium bromide, 1-butyl-3-methylpyridinium bromide, 1-butyl-3-methylpyridinium chloride, 1-butyl-4-methylpyridinium chloride, 1-butyl-4-methylpyridinium hexafluorophosphate, 1-butylpyridinium bromide, 1-butylpyridinium chloride, 1-butylpyridinium hexafluorophosphate, 1-butylpyridinium tetrafluoroborate, 4-carbamoyl-1-hexadecylpyridinium chloride, 1-(carbamoylmethyl)pyridinium chloride, 3-carbamoyl-1-methylpyridibium chloride, 4-picolyl chloride hydrochloride, 2-(chloromethyl)pyridine hydrochloride, 3-(chloromethyl)pyridine hydrochloride, 2-chloro-1-methylpyridinium iodide, 2-chloro-1-methylpyridinium p-toluenesulfonate, 4-chloropyridine hydrochloride, cetylpyridinium chloride, 1-cyano-4-(dimethylamino)pyridinium tetrafluoroborate, 1-(cyanomethyl)pyridinium chloride, cyclobis(paraquat-1,4-phenylene) tetrakis(hexafluorophosphate), 1,1'-dibenzyl-4,4'-bipyridinium dichloride hydrate, 2,6-dichloro-1-fluoropyridinium trifluoromethanesulfonate, 1,1'-difluoro-2,2'-bipyridinium bis(tetrafluoroborate), 1,1'-diheptyl-4,4'-bipyridinium dibromide, 2,6-pyridinediol hydrochloride, 4-dimethylamino-1-neopentylpyridinium chloride, 4-dimethylaminopyridinium bromide perbromide, 4-(dimethylamino)-1-(triphenylmethyl)pyridinium chloride, 1,1'-dimethyl-4,4'-bipyridinium dichloride hydrate, 1,1'-dimethyl-4,4'-bipyridinium dichloride, 1-(dimethylcarbamoyl)-4-(2-sulfoethyl)pyridinium hydroxide intramolecular salt, 2,6-dimethylpyridinium p-toluenesulfonate, 1,1'-di-n-octyl-4,4'-bipyridinium dibromide, 1,1'-diphenyl-4,4'-bipyridinium dichloride, 1-dodecylpyridinium chloride, 1-ethyl-3-(hydroxymethyl)pyridinium ethyl sulfate, 1-ethyl-4-(methoxycarbonyl)pyridinium iodide, 1-ethyl-3-methylpyridinium bis(trifluoromethanesulfonyl)imide, 1-ethyl-3-methylpyridinium ethyl sulfate, 1-ethylpyridinium bromide, 1-ethylpyridinium chloride, 1-fluoro-2,6-dichloropyridinium tetrafluoroborate, 2-fluoro-1-methylpyridinium p-toluenesulfonate, 1-fluoropyridinium pyridine heptafluorodiborate, 1-fluoropyridinium tetrafluoroborate, 1-fluoropyridinium trifluoromethanesulfonate, 1-fluoro-2,4,6-trimethylpyridinium tetrafluoroborate, 1-fluoro-2,4,6-trimethylpyridinium trifluoromethanesulfonate, Girard's reagent P, 1-hexadecyl-4-methylpyridinium chloride hydrate, hexadecylpyridinium bromide hydrate, hexadecylpyridinium chloride monohydrate, isonicotinoyl chloride hydrochloride, MDEPAP, 1-methylpyridinium-2-aldoxime chloride, 1-methylpyridinium chloride, NDEPAP, 1-octadecyl-4-(4-phenyl-1,3-butadienyl)pyridinium bromide, N-octadecyl-4-stilbazole bromide, 1-(10,12-pentacosadiynyl)pyridinium bromide, 1-phenacylpyridinium bromide, 1,1'-[1,4-phenylenebis(methylene)]bis(4,4'-bipyridinium) bis(hexafluorophosphate), 1,1'-[1,4-phenylenebis (methylene)]bis(4,4'-bipyridinium)dibromide, N-phenylnicotinamide hydrochloride, 1-propylpyridinium chloride, pyridine-2-carbonyl chloride hydrochloride, pyridine-2-carboxylic acid hydrochloride, pyridine hydrobromide, pyridine hydrochloride, pyridinium bromide perbromide, pyridinium chlorochromate, pyridinium dichromate, pyridinium fluorochromate, pyridinium 3-nitrobenzenesulfonate, pyridinium poly(hydrogen fluoride), pyridinium p-toluenesulfonate, pyridinium trifluoromethanesulfonate, pyridostigmine bromide, pyridoxamine dihydrochloride monohydrate, pyridoxine hydrochloride, 3-pyridylacetic acid hydrochloride, 2-pyridylacetic acid hydrochloride, 1-(4-pyridyl)pyridinium chloride hydrochloride hydrate, 1-(3-sulfopropyl)pyridinium hydroxide intramolecular salt, $\alpha,\beta,\gamma,\delta$-tetrakis(1-methylpyridinium-4-yl)porphyrin p-toluenesulfonate, 1-(trifluoroacetyl)-4-(dimethylamino) pyridinium trifluoroacetate, 1-methylpyridinium-3-carboxylic acid hydrochloride, and 2,4,6-trimethylpyridinium p-toluenesulfonate.

Specific examples of the pyrrolidinium compounds include 1-butyl-1-methylpyrrolidinium bromide, 1-butyl-1-methylpyrrolidinium chloride, 1-butyl-1-propylpyrrolidinium bromide and 1-butyl-1-propylpyrrolidinium chloride.

A specific example of the piperidinium compounds is 1-butyl-1-methylpiperidinium bromide.

Specific examples of the morpholinium compounds include 4-propyl-4-methylmorpholinium chloride, 4-(2-methoxyethyl)-4-methylmorpholinium chloride, 4-propyl-4-methylmorpholinium bromide, 4-(2-methoxyethyl)-4-methylmorpholinium bromide, 4-propyl-4-methylmorpholinium hydroxide, and 4-(2-methoxyethyl)-4-methylmorpholinium hydroxide.

Specific examples of the quaternary ammonium compounds include fluorides such as propyltrimethylammonium chloride, diethyl-2-methoxyethylmethylammonium fluoride, methyltrioctylammonium fluoride, cyclohexyltrimethylammonium fluoride and 2-hydroxyethyltrimethylammonium fluoride; chlorides such as propyltrimethylammonium chloride, diethyl-2-methoxyethylmethylammonium chloride, methyltrioctylammonium chloride, cyclohexyltrimethylammonium chloride and 2-hydroxyethyltrimethylammonium chloride; bromides such as propyltrimethylammonium bromide, diethyl-2-methoxyethylmethylammonium bromide, methyltrioctylammonium bromide, cyclohexyltrimethylammonium bromide and 2-hydroxyethyltrimethylammonium bromide; iodides such as propyltrimethylammonium iodide, diethyl-2-methoxyethylmethylammonium iodide, methyltrioctylammonium iodide, cyclohexyltrimethylammonium iodide and 2-hydroxyethyltrimethylammonium iodide; hydroxides such as propyltrimethylammonium hydroxide, diethyl-2-methoxyethylmethylammonium hydroxide, methyltrioctylammonium hydroxide, cyclohexyltrimethylammonium hydroxide and 2-hydroxyethyltrimethylammonium hydroxide; acetates such as propyltrimethylammonium acetate, diethyl-2-methoxyethylmethylammonium acetate, methyltrioctylammonium acetate, cyclohexyltrimethylammonium acetate and 2-hydroxyethyltrimethylammonium acetate; and hydrogen sulfates such as propyltrimethylammonium hydrogen sulfate, diethyl-2-methoxyethylmethylammonium hydrogen sulfate, methyltrioctylammonium hydrogen sulfate, cyclohexyltrimethylammonium hydrogen sulfate and 2-hydroxyethyltrimethylammonium hydrogen sulfate.

Specific examples of the phosphonium compounds include acetonyltriphenylphosphonium chloride, allyltriphenylphosphonium bromide, allyltriphenylphosphonium chloride, amyltriphenylphosphonium bromide, 1H-benzotriazol-1-yloxy-tripyrrolidinophosphonium hexafluorophosphate, 1H-benzotriazol-1-yloxy-tris(dimethylamino)phosphonium hexafluorophosphate, benzyltriphenylphosphonium bromide, benzyltriphenylphosphonium chloride, (bromomethyl)triphenylphosphonium bromide, 3-bromopropyltriphenylphosphonium bromide, trans-2-butene-1,4-bis(triphenylphosphonium chloride), butyltriphenylphosphonium bromide, (4-carboxybutyl)triphenylphosphonium bromide, (3-carboxypropyl)triphenylphosphonium bromide, (4-chlorobenzyl)triphenylphosphonium chloride, (2-chlorobenzyl)triphenylphosphonium chloride, (chloromethyl)triphenylphosphonium chloride, cinnamyltriphenylphosphonium bromide, (cyanomethyl)triphenylphosphonium chloride, cyclopropyltriphenylphosphonium bromide, di-tert-butylmethylphosphonium tetraphenylborate, (2,4-dichlorobenzyl)triphenylphosphonium chloride, 2-dimethylaminoethyltriphenylphosphonium bromide, 2-(1,3-dioxan-2-yl)ethyltriphenylphosphonium bromide, 2-(1,3-dioxolan-2-yl)ethyltriphenylphosphonium bromide, (1,3-dioxolan-2-yl)methyltriphenylphosphonium bromide, 4-ethoxybenzyltriphenylphosphonium bromide, ethoxycarbonylmethyl(triphenyl)phosphonium bromide, ethyltriphenylphosphonium bromide, ethyltriphenylphosphonium iodide, (formylmethyl)triphenylphosphonium chloride, heptyltriphenylphosphonium bromide, hexyltriphenylphosphonium bromide, (2-hydroxybenzyl)triphenylphosphonium bromide, isopropyltriphenylphosphonium iodide, methoxycarbonylmethyl(triphenyl)phosphonium bromide, (methoxymethyl)triphenylphosphonium chloride, (N-methyl-N-phenylamino)triphenylphosphonium iodide, methyltriphenylphosphonium bromide, methyltriphenylphosphonium iodide, (1-naphthylmethyl)triphenylphosphonium chloride, (4-nitrobenzyl)triphenylphosphonium bromide, μ-oxobis[tris(dimethylamino)phosphonium] bis(tetrafluoroborate), phenacyltriphenylphosphonium bromide, tetrabutylphosphonium benzotriazolate, tetrabutylphosphonium bis(1,3-dithiole-2-thione-4,5-dithiolate) nickel(III) complex, tetrabutylphosphonium bromide, tetrabutylphosphonium chloride, tetrabutylphosphonium hexafluorophosphate, tetrabutylphosphonium hydroxide, tetrabutylphosphonium tetrafluoroborate, tetrabutylphosphonium tetraphenylborate, tetraethylphosphonium bromide, tetraethylphosphonium hexafluorophosphate, tetraethylphosphonium tetrafluoroborate, tetrakis(hydroxymethyl)phosphonium chloride, tetrakis(hydroxymethyl)phosphonium sulfate, tetra-n-octylphosphonium bromide, tetraphenylphosphonium bromide, tetraphenylphosphonium chloride, tetraphenylphosphonium iodide, tetraphenylphosphonium tetraphenylborate, tetraphenylphosphonium tetra-p-tolylborate, tributyl(cyanomethyl)phosphonium chloride, tributyl(1,3-dioxolan-2-ylmethyl)phosphonium bromide, tributyldodecylphosphonium bromide, tributylhexadecylphosphonium bromide, tributylmethylphosphonium iodide, tributyl-n-octylphosphonium bromide, tri-tert-butylphosphonium tetrafluoroborate, tri-tert-butylphosphonium tetraphenylborate, tricyclohexylphosphonium tetrafluoroborate, 2-(trimethylsilyl)ethoxymethyltriphenylphosphonium chloride, (2-trimethylsilylethyl)triphenylphosphonium iodide, (3-trimethylsilyl-2-propyl)triphenylphosphonium bromide, triphenylpropargylphosphonium bromide, triphenylpropylphosphonium bromide, triphenyl(tetradecyl)phosphonium bromide, and triphenylvinylphosphonium bromide.

Further examples include organic phosphine compounds such as trimethylphosphine, triethylphosphine, tributylphosphine and triphenyl phosphine, which can give rise to phosphonium cations.

Specific examples of the sulfonium compounds include dimethylsulfoniopropionate, trimethylsulfonyl chloride, trimethylsulfonyl bromide, and trimethylsulfonyl iodide.

Specific examples of the guanidinium compounds include guanidinium chloride, 2-ethyl-1,1,3,3-tetramethylguanidinium chloride, guanidinium bromide, 2-ethyl-1,1,3,3-tetramethylguanidinium bromide, guanidinium hydroxide, and 2-ethyl-1,1,3,3-tetramethylguanidinium hydroxide.

Specific examples of the isouronium compounds include 2-ethyl-1,1,3,3-tetramethylisouronium chloride, 2-ethyl-1,1,3,3-tetramethylisouronium bromide, and 2-ethyl-1,1,3,3-tetramethylisouronium hydroxide.

Specific examples of the isouronium compounds include 2-ethyl-1,1,3,3-tetramethylisothiouronium chloride, 2-ethyl-1,1,3,3-tetramethylisothiouronium bromide, and 2-ethyl-1,1,3,3-tetramethylisothiouronium hydroxide.

Among these compounds, onium hydroxide compounds are preferable. By using an onium hydroxide compound, ammonia is produced as a by-product of the reaction, and therefore by removing this ammonia under reduced pressure, the equilibrium can be adjusted to a state that promotes the reaction. By using an onium compound, the inorganic salt by-products can be removed by filtration and water washing, meaning the product can be easily purified.

The amount used of the onium compound is preferably from 0.3 mol to 10 mol, and more preferably from 0.3 mol to 5 mol, per 1 mol of the compound [II].

Examples of the organic amine compound used in the cation exchange reaction include tertiary amines such as trimethylamine, triethylamine and tributylamine, cyclic amines such as 1,4-diazabicyclo[2.2.2]octane, tertiary amine salts such as trimethylamine hydrochloride, triethylamine hydrochloride, tributylamine hydrochloride, 1,4-diazabicyclo[2.2.2]octane hydrochloride, trimethylamine hydrobromide, triethylamine hydrobromide and tributylamine hydrobromide, and cyclic amine salts such as 1,4-diazabicyclo[2.2.2]octane hydrobromide.

Among these compounds, tertiary amines and cyclic amines are preferable. By using a tertiary amine or a cyclic amine, ammonia is produced as a by-product in the cation exchange reaction, and therefore by removing this ammonia under reduced pressure, the equilibrium can be adjusted to a state that promotes the reaction. On the other hand, the inorganic salt by-products that are produced when using a tertiary amine or a cyclic amine can be removed by filtration and water washing, meaning the product can be easily purified.

The amount used of the organic amine compound is preferably from 0.3 mol to 10 mol, and more preferably from 0.3 mol to 5 mol, per 1 mol of the compound [II].

There are no particular limitations on the organic solvent used in the cation exchange reaction. Examples of preferred solvents include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methylsulfolane, dimethylsulfoxide, N,N-dimethylformamide, N-methyl oxazolidinone, acetonitrile, valeronitrile, benzonitrile, ethyl acetate, isopropyl acetate, butyl acetate, nitromethane and nitrobenzene. Among these solvents, acetonitrile, ethyl acetate, isopropyl acetate and butyl acetate can be used in both the reaction between the compound [I] and hydrogen fluoride, and the cation exchange reaction of the compound [II], and therefore no solvent substitution is required, and the above reactions can be performed consecutively within the same solvent, which is preferable.

There are no particular limitations on the temperature during the cation exchange reaction, but the temperature is preferably from 0° C. to 200° C., and more preferably from 10° C. to 100° C. The time required for the reaction varies depending on the reaction scale, but is preferably from 0.1 hours to 48 hours, and more preferably from 0.5 hours to 24 hours.

Although the reaction can be performed under normal pressure, in those cases where a compound having a hydroxide ion is used during the cation exchange, performing the reaction under reduced pressure enables the ammonia that is produced as a by-product to be removed, thereby tilting the equilibrium and facilitating synthesis of the product. When the reaction is performed under reduced pressure, although there are no particular limitations on the reaction pressure, a pressure within a range from atmospheric pressure to 0.01 torr is preferable, and a pressure under which the solvent can be refluxed at a temperature within a range from 0° C. to 100° C. is more preferable.

The reaction vessel may be made of glass or a resin such as a fluororesin or a polyethylene resin, but if the value of p in the fluorinating agent represented by formula [III] is 1 or greater, then the reaction yield decreases if a glass reaction vessel is used, and therefore a resin vessel is preferable, and a fluororesin vessel is particularly desirable.

By performing the above cation exchange reaction, the compound [IV] can be obtained. The compound [IV] is a fluorosulfonylimide salt represented by formula [IV].

[Chemical Formula 8]

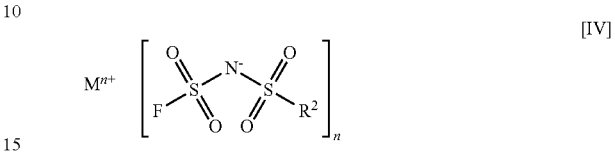

In formula [IV], $M^{n+}$ represents a metal cation or an onium cation (excluding $NH_4^+$), n corresponds with the valency of the metal cation or the onium cation (excluding $NH_4^+$) and is an integer of 1 to 4 (and preferably an integer of 1 to 3), and $R^2$ is the same as defined above in formula [II].

Although there are no particular limitations on the metal cation, an alkali metal cation is preferable. Examples of the alkali metal cation include a lithium cation, sodium cation, potassium cation, rubidium cation and cesium cation. Of these, a lithium cation, sodium cation or potassium cation is preferable.

Examples of the onium cation (excluding $NH_4^+$) include a phosphonium cation, oxonium cation, sulfonium cation, fluoronium cation, chloronium cation, bromonium cation, iodonium cation, selenonium cation, telluronium cation, arsonium cation, stibonium cation, bismutonium cation; iminium cation, diazenium cation, nitronium cation, diazonium cation, nitrosonium cation, hydrazonium cation, diazenium dication, diazonium dication, imidazolium cation, pyridinium cation, quaternary ammonium cation, tertiary ammonium cation, secondary ammonium cation, primary ammonium cation, piperidinium cation, pyrrolidinium cation, morpholinium cation, pyrazolium cation, guanidinium cation, isouronium cation and isothiouronium cation.

The onium cation is preferably an onium cation having an organic group, namely an organic onium cation. Examples of the organic group include saturated and unsaturated hydrocarbon groups. The saturated or unsaturated hydrocarbon group may be linear, branched or cyclic. The number of carbon atoms that constitute the saturated or unsaturated hydrocarbon group is preferably from 1 to 18, and more preferably from 1 to 8. The atoms or atom groupings that constitute the organic group preferably include a hydrogen atom, fluorine atom, amino group, imino group, amide group, ether group, hydroxyl group, ester group, carboxyl group, carbamoyl group, cyano group, sulfone group, sulfide group, nitrogen atom, oxygen atom or sulfur atom; and more preferably include a hydrogen atom, fluorine atom, ether group, hydroxyl group, cyano group or sulfone group. The organic group may have only one of these atoms or atom groupings, or may have two or more of the atoms or atom groupings. When two or more organic groups are bonded, bonds may be formed between the main structures of the organic groups, between the main structures of the organic groups and an aforementioned atom grouping, or between atom groupings described above.

Examples of the onium cation having an organic group include imidazolium cations such as a 1,3-dimethylimidazolium cation, 1-ethyl-3-methylimidazolium cation, 1-propyl-3-methylimidazolium cation, 1-butyl-3-methylimidazolium cation, 1-pentyl-3-methylimidazolium cation, 1-hexyl-3-methylimidazolium cation, 1-heptyl-3-methylimidazolium cation, 1-octyl-3-methylimidazolium cation, 1-decyl-3-methylimidazolium cation, 1-tetradecyl-3-methylimidazolium cation, 1-hexadecyl-3-methylimidazolium cation, 1-octadecyl-3-methylimidazolium cation, 1-allyl-3-ethylimidazolium cation, 1-allyl-3-butylimidazolium cation, 1,3-diallylimidazolium cation, 1-ethyl-2,3-dimethylimidazolium cation, 1-butyl-2,3-dimethylimidazolium cation, 1-hexyl-2,3-methylimidazolium cation, and 1-hexadecyl-2,3-methylimidazolium cation;

pyridinium cations such as a 1-ethylpyridinium cation, 1-butylpyridinium cation, 1-hexylpyridinium cation, 1-octylpyridinium cation, 1-ethyl-3-methylpyridinium cation, 1-ethyl-3-hydroxymethylpyridinium cation, 1-butyl-3-methylpyridinium cation, 1-butyl-4-methylpyridinium cation, 1-octyl-4-methylpyridinium cation, 1-butyl-3,4-dimethylpyridinium cation, and 1-butyl-3,5-dimethylpyridinium cation;

quaternary ammonium cations such as a tetramethylammonium cation, tetraethylammonium cation, tetrapropylammonium cation, tetrabutylammonium cation, tetraheptylammonium cation, tetrahexylammonium cation, tetraoctylammonium cation, triethylmethylammonium cation, propyltrimethylammonium cation, diethyl-2-methoxyethylmethylammonium cation, methyltrioctylammonium cation, cyclohexyltrimethylammonium cation, 2-hydroxyethyltrimethylammonium cation, trimethylphenylammonium cation, benzyltrimethylammonium cation, benzyltributylammonium cation, benzyltriethylammonium cation, dimethyldistearylammonium cation, diallyldimethylammonium cation, 2-methoxyethoxymethyltrimethylammonium cation, and tetrakis(pentafluoroethyl)ammonium cation;

tertiary ammonium cations such as a trimethylammonium cation, triethylammonium cation, tributylammonium cation, diethylmethylammonium cation, dimethylethylammonium cation, dibutylmethylammonium cation, and 4-aza-1-azoniabicyclo[2.2.2]octane cation;

secondary ammonium cations such as a dimethylammonium cation, diethylammonium cation, and dibutylammonium cation;

primary ammonium cations such as a methylammonium cation, ethylammonium cation, butylammonium cation, hexylammonium cation, and octylammonium cation;

organic ammonium cations such as an N-methoxytrimethylammonium cation, N-ethoxytrimethylammonium cation, and N-propoxytrimethylammonium cation;

piperidinium cations such as a 1-propyl-1-methylpiperidinium cation and 1-(2-methoxyethyl)-1-methylpiperidinium cation;

pyrrolidinium cations such as a 1-propyl-1-methylpyrrolidinium cation, 1-butyl-1-methylpyrrolidinium cation, 1-hexyl-1-methylpyrrolidinium cation, and 1-octyl-1-methylpyrrolidinium cation;

morpholinium cations such as a 4-propyl-4-methylmorpholinium cation and 4-2-methoxyethyl)-4-methylmorpholinium cation;

pyrazolium cations such as a 2-ethyl-1,3,5-trimethylpyrazolium cation, 2-propyl-1,3,5-trimethylpyrazolium cation, 2-butyl-1,3,5-trimethylpyrazolium cation, and 2-hexyl-1,3,5-trimethylpyrazolium cation; guanidinium cations such as a guanidinium cation and a 2-ethyl-1,1,3,3-tetramethylguanidinium cation;

sulfonium cations such as a trimethylsulfonium cation;

phosphonium cations such as a trihexyltetradecylphosphonium cation;

isouronium cations such as a 2-ethyl-1,1,3,3-tetramethylisouronium cation; and isothiouronium cations such as a 2-ethyl-1,1,3,3-tetramethylisothiouronium cation.

Among these, the onium cation preferably contains no metal elements that degrade electrolyte properties and the like. Specifically, imidazolium cations such as a 1,3-dimethylimidazolium cation, 1-ethyl-3-methylimidazolium cation, 1-butyl-3-methylimidazolium cation, 1-hexyl-3-methylimidazolium cation, 1-octyl-3-methylimidazolium cation, 1-allyl-3-ethylimidazolium cation, 1-allyl-3-butylimidazolium cation, 1,3-diallylimidazolium cation, 1-ethyl-2,3-dimethylimidazolium cation, 1-butyl-2,3-dimethylimidazolium cation, and 1-hexyl-2,3-dimethylimidazolium cation; and organic ammonium cations such as a propyltrimethylammonium cation, diethyl-2-methoxyethylmethylammonium cation, methyltrioctylammonium cation, cyclohexyltrimethylammonium cation, 2-hydroxyethyltrimethylammonium cation, trimethylammonium cation, triethylammonium cation, tributylammonium cation, and 4-aza-1-azoniabicyclo[2.2.2]octane cation are preferable.

Specific examples of the compound [IV] include lithium di(fluorosulfonyl)imide, lithium N-(fluorosulfonyl)-N-(trifluoromethylsulfonyl)imide, lithium N-(fluorosulfonyl)-N-(pentafluoroethylsulfonyl)imide, and lithium N-(fluorosulfonyl)-N-(perfluoro-n-propysulfonyl)imide; potassium di(fluorosulfonyl)imide, potassium N-(fluorosulfonyl)-N-(trifluoromethylsulfonyl)imide, potassium N-(fluorosulfonyl)-N-(pentafluoroethylsulfonyl)imide, and potassium N-(fluorosulfonyl)-N-(perfluoro-n-propylsulfonyl)imide; sodium di(fluorosulfonyl)imide, sodium N-(fluorosulfonyl)-N-(trifluoromethylsulfonyl)imide, sodium N-(fluorosulfonyl)-N-(pentafluoroethylsulfonyl)imide, and sodium N-(fluorosulfonyl)-N-(perfluoro-n-propylsulfonyl)imide;

1,3-dimethylimidazolium di(fluorosulfonyl)imide, 1,3-dimethylimidazolium N-(fluorosulfonyl)-N-(trifluoromethylsulfonyl)imide, 1,3-dimethylimidazolium N-(fluorosulfonyl)-N-(pentafluoroethylsulfonyl)imide, and 1,3-dimethylimidazolium N-(fluorosulfonyl)-N-(perfluoro-n-propylsulfonyl)imide; 1-ethyl-3-methylimidazolium di(fluorosulfonyl)imide, 1-ethyl-3-methylimidazolium N-(fluorosulfonyl)-N-(trifluoromethylsulfonyl)imide, 1-ethyl-3-methylimidazolium N-(fluorosulfonyl)-N-(pentafluoroethylsulfonyl)imide, and 1-ethyl-3-methylimidazolium N-(fluorosulfonyl)-N-(perfluoro-n-propylsulfonyl)imide; 1-butyl-3-methylimidazolium di(fluorosulfonyl)imide, 1-butyl-3-methylimidazolium N-(fluorosulfonyl)-N-(trifluoromethylsulfonyl)imide, 1-butyl-3-methylimidazolium N-(fluorosulfonyl)-N-(pentafluoroethylsulfonyl)imide, and 1-butyl-3-methylimidazolium N-(fluorosulfonyl)-N-(perfluoro-n-propylsulfonyl)imide; 1-hexyl-3-methylimidazolium di(fluorosulfonyl)imide, 1-hexyl-3-methylimidazolium N-(fluorosulfonyl)-N-(trifluoromethylsulfonyl)imide, 1-hexyl-3-methylimidazolium N-(fluorosulfonyl)-N-(pentafluoroethylsulfonyl)imide, and 1-hexyl-3-methylimidazolium N-(fluorosulfonyl)-N-(perfluoro-n-propylsulfonyl)imide;

1-octyl-3-methylimidazolium di(fluorosulfonyl)imide, 1-octyl-3-methylimidazolium N-(fluorosulfonyl)-N-(trifluoromethylsulfonyl)imide, 1-octyl-3-methylimidazolium N-(fluorosulfonyl)-N-(pentafluoroethylsulfonyl)imide, and 1-octyl-3-methylimidazolium N-(fluorosulfonyl)-N-(perfluoro-n-propylsulfonyl)imide; 1-allyl-3-ethylimidazolium di(fluorosulfonyl)imide, 1-allyl-3-ethylimidazolium N-(fluorosulfonyl)-N-(trifluoromethylsulfonyl)imide, 1-allyl-3-ethylimidazolium N-(fluorosulfonyl)-N-(pentafluoroethylsulfonyl)imide, and 1-allyl-3-ethylimidazolium N-(fluorosulfonyl)-N-(perfluoro-n-propylsulfonyl)imide;

1-allyl-3-butylimidazolium di(fluorosulfonyl)imide, 1-allyl-3-butylimidazolium N-(fluorosulfonyl)-N-(trifluoromethylsulfonyl)imide, 1-allyl-3-butylimidazolium N-(fluorosulfonyl)-N-(pentafluoroethylsulfonyl)imide, and 1-allyl-3-butylimidazolium N-(fluorosulfonyl)-N-(perfluoro-n-propylsulfonyl)imide; 1,3-diallylimidazolium di(fluorosulfonyl)imide, N-(fluorosulfonyl)-N-(trifluoromethylsulfonyl)imide, 1,3-diallylimidazolium N-(fluorosulfonyl)-N-(pentafluoroethylsulfonyl)imide, and 1,3-diallylimidazolium N-(fluorosulfonyl)-N-(perfluoro-n-propylsulfonyl)imide;

1-ethyl-2,3-dimethylimidazolium di(fluorosulfonyl)imide, 1-ethyl-2,3-dimethylimidazolium N-(fluorosulfonyl)-N-(trifluoromethylsulfonyl)imide, 1-ethyl-2,3-dimethylimidazolium N-(fluorosulfonyl)-N-(pentafluoroethylsulfonyl)imide, and 1-ethyl-2,3-dimethylimidazolium N-(fluorosulfonyl)-N-(perfluoro-n-propylsulfonyl)imide;

1-butyl-2,3-dimethylimidazolium di(fluorosulfonyl)imide, 1-butyl-2,3-dimethylimidazolium N-(fluorosulfonyl)-N-(trifluoromethylsulfonyl)imide, 1-butyl-2,3-dimethylimidazolium N-(fluorosulfonyl)-N-(pentafluoroethylsulfonyl)imide, and 1-butyl-2,3-dimethylimidazolium N-(fluorosulfonyl)-N-(perfluoro-n-propylsulfonyl)imide; 1-hexyl-2,3-dimethylimidazolium di(fluorosulfonyl)imide, 1-hexyl-2,3-dimethylimidazolium N-(fluorosulfonyl)-N-(trifluoromethylsulfonyl)imide, 1-hexyl-2,3-dimethylimidazolium N-(fluorosulfonyl)-N-(pentafluoroethylsulfonyl)imide, and 1-hexyl-2,3-dimethylimidazolium N-(fluorosulfonyl)-N-(perfluoro-n-propylsulfonyl)imide;

1-butylpyridinium di(fluorosulfonyl)imide, 1-butylpyridinium N-(fluorosulfonyl)-N-(trifluoromethylsulfonyl)imide, 1-butylpyridinium N-(fluorosulfonyl)-N-(pentafluoroethylsulfonyl)imide, and 1-butylpyridinium N-(fluorosulfonyl)-N-(perfluoro-n-propylsulfonyl)imide; 1-hexylpyridinium di(fluorosulfonyl)imide, 1-hexylpyridinium N-(fluorosulfonyl)-N-(trifluoromethylsulfonyl)imide, 1-hexylpyridinium N-(fluorosulfonyl)-N-(pentafluoroethylsulfonyl)imide, and 1-hexylpyridinium N-(fluorosulfonyl)-N-(perfluoro-n-propylsulfonyl)imide;

1-octylpyridinium di(fluorosulfonyl)imide, 1-octylpyridinium N-(fluorosulfonyl)-N-(trifluoromethylsulfonyl)imide, 1-octylpyridinium N-(fluorosulfonyl)-N-(pentafluoroethylsulfonyl)imide, and 1-octylpyridinium N-(fluorosulfonyl)-N-(perfluoro-n-propylsulfonyl)imide; 1-ethyl-3-methylpyridinium di(fluorosulfonyl)imide, 1-ethyl-3-methylpyridinium N-(fluorosulfonyl)-N-(trifluoromethylsulfonyl)imide, 1-ethyl-3-methylpyridinium N-(fluorosulfonyl)-N-(pentafluoroethylsulfonyl)imide, and 1-ethyl-3-methylpyridinium N-(fluorosulfonyl)-N-(perfluoro-n-propylsulfonyl)imide;

1-butyl-3-methylpyridinium di(fluorosulfonyl)imide, 1-butyl-3-methylpyridinium N-(fluorosulfonyl)-N-(trifluoromethylsulfonyl)imide, 1-butyl-3-methylpyridinium N-(fluorosulfonyl)-N-(pentafluoroethylsulfonyl)imide, and 1-butyl-3-methylpyridinium N-(fluorosulfonyl)-N-(perfluoro-n-propylsulfonyl)imide; 1-butyl-4-methylpyridinium di(fluorosulfonyl)imide, 1-butyl-4-methylpyridinium N-(fluorosulfonyl)-N-(trifluoromethylsulfonyl)imide, 1-butyl-4-methylpyridinium N-(fluorosulfonyl)-N-(pentafluoroethylsulfonyl)imide, and 1-butyl-4-methylpyridinium N-(fluorosulfonyl)-N-(perfluoro-n-propylsulfonyl)imide;

diethyl-2-methoxyethylmethylammonium di(fluorosulfonyl)imide, diethyl-2-methoxyethylmethylammonium N-(fluorosulfonyl)-N-(trifluoromethylsulfonyl)imide, diethyl-2-methoxyethylmethylammonium N-(fluorosulfonyl)-N-(pentafluoroethylsulfonyl)imide, and diethyl-2-methoxyethylmethylammonium N-(fluorosulfonyl)-N-(perfluoro-n-propylsulfonyl)imide; methyltrioctylammonium di(fluorosulfonyl)imide, methyltrioctylammonium N-(fluorosulfonyl)-N-(trifluoromethylsulfonyl)imide, methyltrioctylammonium N-(fluorosulfonyl)-N-(pentafluoroethylsulfonyl)imide, and methyltrioctylammonium N-(fluorosulfonyl)-N-(perfluoro-n-propylsulfonyl)imide; cyclohexyltrimethylammonium di(fluorosulfonyl)imide, cyclohexyltrimethylammonium N-(fluorosulfonyl)-N-(trifluoromethylsulfonyl)imide, cyclohexyltrimethylammonium N-(fluorosulfonyl)-N-(pentafluoroethylsulfonyl)mide, and cyclohexyltrimethylammonium N-(fluorosulfonyl)-N-(perfluoro-n-propylsulfonyl)imide;

trimethylammonium di(fluorosulfonyl)imide, trimethylammonium N-(fluorosulfonyl)-N-(trifluoromethylsulfonyl)imide, trimethylammonium N-(fluorosulfonyl)-N-(pentafluoroethylsulfonyl)imide, and trimethylammonium N-(fluorosulfonyl)-N-(perfluoro-n-propylsulfonyl)imide; triethylammonium di(fluorosulfonyl)imide, triethylammonium N-(fluorosulfonyl)-N-(trifluoromethylsulfonyl)imide, N-(fluorosulfonyl)-N-(pentafluoroethylsulfonyl)imide, and triethylammonium N-(fluorosulfonyl)-N-(perfluoro-n-propylsulfonyl)imide; tributylammonium di(fluorosulfonyl)imide, tributylammonium N-(fluorosulfonyl)-N-(trifluoromethylsulfonyl)imide, tributylammonium N-(fluorosulfonyl)-N-(pentafluoroethylsulfonyl)imide, and tributylammonium N-(fluorosulfonyl)-N-(perfluoro-n-propylsulfonyl)imide; 4-aza-1-azoniabicyclo[2.2.2]octane di(fluorosulfonyl)imide, 4-aza-1-azoniabicyclo[2.2.2]octane N-(fluorosulfonyl)-N-(trifluoromethylsulfonyl)imide, 4-aza-1-azoniabicyclo[2.2.2]octane N-(fluorosulfonyl)-N-(pentafluoroethylsulfonyl)imide, and 4-aza-1-azoniabicyclo[2.2.2]octane N-(fluorosulfonyl)-N-(perfluoro-n-propylsulfonyl)imide;

1-propyl-1-methylpiperidinium di(fluorosulfonyl)imide, 1-propyl-1-methylpiperidinium N-(fluorosulfonyl)-N-(trifluoromethylsulfonyl)imide, 1-propyl-1-methylpiperidinium N-(fluorosulfonyl)-N-(pentafluoroethylsulfonyl)imide, and 1-propyl-1-methylpiperidinium N-(fluorosulfonyl)-N-(perfluoro-n-propylsulfonyl)imide; 1-propyl-1-methylpyrrolidinium di(fluorosulfonyl)imide, 1-propyl-1-methylpyrrolidinium N-(fluorosulfonyl)-N-(trifluoromethylsulfonyl)imide, 1-propyl-1-methylpyrrolidinium N-(fluorosulfonyl)-N-(pentafluoroethylsulfonyl)imide, and 1-propyl-1-methylpyrrolidinium N-(fluorosulfonyl)-N-(perfluoro-n-propylsulfonyl)imide; 1-butyl-1-methylpyrrolidinium di(fluorosulfonyl)imide, 1-butyl-1-methylpyrrolidinium N-(fluorosulfonyl)-N-(trifluoromethylsulfonyl)imide, 1-butyl-1-methylpyrrolidinium N-(fluorosulfonyl)-N-(pentafluoroethylsulfonyl)imide, and 1-butyl-1-methylpyrrolidinium N-(fluorosulfonyl)-N-(perfluoro-n-propylsulfonyl)imide;

4-propyl-4-methylmorpholinium di(fluorosulfonyl)imide, 4-propyl-4-methylmorpholinium N-(fluorosulfonyl)-N-(trifluoromethylsulfonyl)imide, 4-propyl-4-methylmorpholinium N-(fluorosulfonyl)-N-(pentafluoroethylsulfonyl)imide, and 4-propyl-4-methylmorpholinium N-(fluorosulfonyl)-N-(perfluoro-n-propylsulfonyl)imide; 2-butyl-1,3,5-trimethylpyrazolium di(fluorosulfonyl)imide, 2-butyl-1,3,5-trimethylpyrazolium N-(fluorosulfonyl)-N-(trifluoromethylsulfonyl)imide, 2-butyl-1,3,5-trimethylpyrazolium N-(fluorosulfonyl)-N-(pentafluoroethylsulfonyl)imide, and 2-butyl-1,3,5-trimethylpyrazolium N-(fluorosulfonyl)-N-(perfluoro-n-propylsulfonyl)imide;

2-ethyl-1,1,3,3-tetramethylguanidinium di(fluorosulfonyl)imide, 2-ethyl-1,1,3,3-tetramethylguanidinium N-(fluorosulfonyl)-N-(trifluoromethylsulfonyl)imide, 2-ethyl-1,1,3,3-tetramethylguanidinium N-(fluorosulfonyl)-N-(pentafluoroethylsulfonyl)imide, and 2-ethyl-1,1,3,3-tetramethylguanidinium N-(fluorosulfonyl)-N-(perfluoro-n- propylsulfonyl)imide; trimethylsulfonium di(fluorosulfonyl) imide, trimethylsulfonium N-(fluorosulfonyl)-N-(trifluoromethylsulfonyl)imide, trimethylsulfonium N-(fluorosulfonyl)-N-(pentafluoroethylsulfonyl)imide, and trimethylsulfonium N-(fluorosulfonyl)-N-(perfluoro-n-propylsulfonyl)imide; trihexyltetradecylphosphonium di(fluorosulfonyl)imide, trihexyltetradecylphosphonium N-(fluorosulfonyl)-N-(trifluoromethylsulfonyl)imide, trihexyltetradecylphosphonium N-(fluorosulfonyl)-N-(pentafluoroethylsulfonyl)imide, and trihexyltetradecylphosphonium N-(fluorosulfonyl)-N-(perfluoro-n-propylsulfonyl) imide;

2-ethyl-1,1,3,3-tetramethylisouronium di(fluorosulfonyl) imide, 2-ethyl-1,1,3,3-tetramethylisouronium N-(fluorosulfonyl)-N-(trifluoromethylsulfonyl)imide, 2-ethyl-1,1,3,3-tetramethylisouronium N-(fluorosulfonyl)-N-(pentafluoroethylsulfonyl)imide, and 2-ethyl-1,1,3,3-tetramethylisouronium N-(fluorosulfonyl)-N-(perfluoro-n-propylsulfonyl)imide; 2-ethyl-1,1,3,3-tetramethylisothiouronium di(fluorosulfonyl)imide, 2-ethyl-1,1,3,3-tetramethylisothiouronium N-(fluorosulfonyl)-N-(trifluoromethylsulfonyl)imide, 2-ethyl-1,1,3,3-tetramethylisothiouronium N-(fluorosulfonyl)-N-(pentafluoroethylsulfonyl)imide, and 2-ethyl-1,1,3,3-tetramethylisothiouronium N-(fluorosulfonyl)-N-(perfluoro-n-propylsulfonyl)imide.

The compound [IV] obtained in accordance with the production process of the present invention contains a smaller amount of contamination by metal impurities that degrade the electrolyte properties and the like when compared with compounds obtained by conventional methods, and can therefore be used favorably as a material for an ion conductor used in forming primary cells, secondary cells such as a lithium ion secondary cell, and electrochemical devices such as electrolytic capacitors, electrical double-layer capacitors, fuel cells, solar cells and electrochromic elements.

EXAMPLES

The present invention is described below in further detail based on a series of examples. However, the present invention is in no way limited by the following examples, and appropriate changes can, of course, be made while still conforming with the purport of the present invention, and such changes are all deemed to be included within the technical scope of the present invention.

Synthesis Example 1

Synthesis of di(chlorosulfonyl)imide

A 500 ml reaction vessel equipped with a stirrer, a thermometer and a reflux condenser was charged with 123.9 g (1.10 mol) of chlorosulfonic acid (ClSO$_3$H) and 98.1 g (0.70 mol) of chlorosulfonyl isocyanate. The temperature of this mixed liquid was raised to 130° C. under stirring over a period of 2.5 hours, and reaction was performed at this temperature for 9 hours. Following completion of the reaction, distillation was performed under reduced pressure, and a fraction was collected at 98.5° C. to 101° C./4.2 torr. Di(chlorosulfonyl)imide was obtained as a colorless transparent liquid in an amount of 77.9 g (0.36 mol).

Example 1

Synthesis of Ammonium di(fluorosulfonyl)imide

A fluororesin reaction vessel was charged with 1.07 g (5.0 mmol) of the di(chlorosulfonyl)imide obtained in Synthesis Example 1. Then, 10 ml of acetonitrile and 0.89 g (24.0 mmol) of NH$_4$F were added to the vessel, and a reaction was performed at 80 to 84° C. for 4 hours under reflux. Following completion of the reaction, the reaction mixture was cooled to room temperature, and the insoluble matter was removed by filtration and washed with 10 ml of acetonitrile. Subsequently, the solvent was removed by distillation under reduced pressure. Quantitative analysis of the obtained substance by $^{19}$F-NMR confirmed that the product contained 0.95 g (4.8 mmol) of ammonium di(fluorosulfonyl)imide.

Example 2

Synthesis of Ammonium di(fluorosulfonyl)imide

A fluororesin reaction vessel was charged with 1.07 g (5.0 mmol) of the di(chlorosulfonyl)imide obtained in Synthesis Example 1. Then, 10 ml of acetonitrile and 1.37 g (24.0 mmol) of NH$_4$F HF were added to the vessel, and a reaction was performed at 80 to 84° C. for 4 hours under reflux. Following completion of the reaction, the reaction mixture was cooled to room temperature, and the insoluble matter was removed by filtration and washed with 10 ml of acetonitrile. Subsequently, the solvent was removed by distillation under reduced pressure. Quantitative analysis of the obtained substance by $^{19}$F-NMR confirmed that the product contained 0.94 g (4.8 mmol) of ammonium di(fluorosulfonyl)imide.

Example 3

Synthesis of Potassium di(fluorosulfonyl)imide

A reaction vessel was charged with 1.98 g (10.0 mmol) of ammonium di(fluorosulfonyl)imide, 10 ml of butyl acetate, and a 20% aqueous solution containing 1.40 g (25.0 mmol) of potassium hydroxide, and the mixture was refluxed at 65 torr and 37° C. for one hour. The reaction liquid was then cooled to 25° C. Subsequently, a liquid-liquid separation was performed, and the water phase was extracted 3 times with 10 ml samples of butyl acetate. The organic phases obtained in the extraction operations were combined, and the solvent was then removed from the organic phase by distillation under reduced pressure, yielding 1.93 g of potassium di(fluorosulfonyl)imide. The results of quantitative analysis by cation chromatography revealed that the entire product was composed of the potassium salt, and contained no ammonium ions.

Example 4

Synthesis of Lithium di(fluorosulfonyl)imide

To 3.8 g (18.9 mmol) of ammonium di(fluorosulfonyl) imide were added 38 ml of butyl acetate, 2.4 g (56.7 mmol) of lithium hydroxide monohydrate and 14.3 ml of water, and the mixture was refluxed under heat at 75 torr and 40° C. for one hour. The reaction liquid was then cooled to 25° C. Subsequently, a liquid-liquid separation was performed, and the water phase was extracted 3 times with 19 ml samples of butyl acetate. The organic phases obtained in the extraction operations were combined, and then washed with 1.5 ml of water. Subsequently, the solvent was removed by distillation under reduced pressure, yielding 3.4 g of lithium di(fluorosulfonyl) imide. The results of quantitative analysis by cation chromatography revealed that the entire product was composed of the lithium salt, and contained no ammonium ions.

Example 5

Synthesis of Sodium di(fluorosulfonyl)imide

To 15.8 g (79.8 mmol) of ammonium di(fluorosulfonyl) imide were added 160 ml of butyl acetate and a 20% aqueous solution containing 40.0 g (200.0 mmol) of sodium hydroxide, and the mixture was refluxed under heat at 65 torr and 37° C. for one hour. The reaction liquid was then cooled to 25° C. Subsequently, a liquid-liquid separation was performed, and the water phase was extracted 3 times with 80 ml samples of butyl acetate. The organic phases obtained in the extraction operations were combined, and the solvent was then removed from the organic phase by distillation under reduced pressure. Then, 80 ml of methylene chloride was added, and the mixture was stirred at room temperature for 15 minutes. Subsequently, the crystals were collected by filtration. The thus obtained crystals were washed with 80 ml of methylene chloride, and were then dried at room temperature under reduced pressure. Sodium di(fluorosulfonyl)imide was obtained in an amount of 13.4 g. The results of quantitative analysis by cation chromatography revealed that the entire product was composed of the sodium salt, and contained no ammonium ions.

INDUSTRIAL APPLICABILITY

According to the present invention, fluorosulfonylimide ammonium salts can be manufactured in an industrially efficient manner. Further, by subjecting the thus obtained fluorosulfonylimide ammonium salt to a cation exchange reaction, another fluorosulfonylimide salt containing no metal impurities that degrade electrolyte properties and the like can be manufactured.

The invention claimed is:

1. A process for producing a fluorosulfonylimide ammonium salt of formula [II], the method comprising reacting a compound of formula [I] and a fluorinating agent of formula [III]:

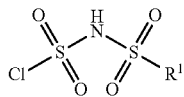
[I]

wherein $R^1$ represents a fluoroalkyl group having 1 to 6 carbon atoms, a fluorine atom, or a chlorine atom, $$NH_4F(HF)_p \quad [III]$$

wherein p represents a real number of 1 to 10,

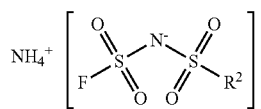
[II]

wherein $R^2$ represents a fluoroalkyl group having 1 to 6 carbon atoms, or a fluorine atom.

2. A process for producing a fluorosulfonylimide salt of formula [IV], the method comprising:
obtaining a fluorosulfonylimide ammonium salt of formula [II] by the process defined in claim 1:

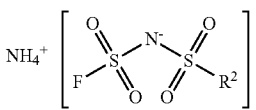
[II]

wherein $R^2$ represents a fluoroalkyl group having 1 to 6 carbon atoms, or a fluorine atom; and
reacting the fluorosulfonylimide ammonium salt of formula [II] with at least one compound selected from the group consisting of metal compounds, onium compounds and organic amine compounds:

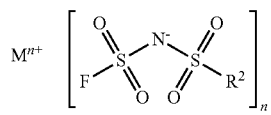
[IV]

wherein $M^{n+}$ represents a metal cation or an onium cation (excluding $NH_4^+$), n corresponds with a valency of the metal cation or the onium cation (excluding $NH_4^+$) and is an integer of 1 to 4, and $R^2$ is as defined above in formula [II].

3. The process for producing a fluorosulfonylimide salt according to claim 2, wherein the at least one compound is selected from the group consisting of alkali metal compounds, onium compounds and organic amine compounds.

4. The process of producing a fluorosulfonylimide salt according to claim 3, wherein:
the reaction of the fluorosulfonylimide ammonium salt of formula [II] with at least one compound is performed under reduced pressure; and
the at least one compound is an alkali metal hydroxide.

* * * * *